(12) United States Patent
Peng et al.

(10) Patent No.: US 9,820,721 B2
(45) Date of Patent: Nov. 21, 2017

(54) ASPIRATION AND BIOPSY NEEDLE APPARATUS AND DEVICES AND APPLICATIONS THEREOF

(71) Applicant: Beta Pharma, Inc., Princeton, NJ (US)

(72) Inventors: Jirong Peng, Mequon, WI (US); Don Zhang, Plainsboro, NJ (US)

(73) Assignee: Beta Pharma, Inc., Wilmington, DE (US)

( * ) Notice: Subject to any disclaimer, the term of this patent is extended or adjusted under 35 U.S.C. 154(b) by 138 days.

(21) Appl. No.: 14/694,896

(22) Filed: Apr. 23, 2015

(65) Prior Publication Data

US 2015/0305724 A1    Oct. 29, 2015

Related U.S. Application Data

(60) Provisional application No. 61/983,213, filed on Apr. 23, 2014.

(51) Int. Cl.
*A61B 5/00* (2006.01)
*A61B 10/02* (2006.01)
*A61B 10/00* (2006.01)

(52) U.S. Cl.
CPC ...... *A61B 10/0283* (2013.01); *A61B 10/0096* (2013.01); *A61B 2010/0258* (2013.01)

(58) Field of Classification Search
CPC ... A61B 5/1405; A61B 5/1433; A61B 5/1438; A61B 5/1444; A61B 10/0045; A61B 10/02; A61B 10/0283; A61B 2010/045; A61B 10/0096; A61B 2010/0258
USPC ................................................. 600/565, 571
See application file for complete search history.

(56) References Cited

U.S. PATENT DOCUMENTS

| | | | |
|---|---|---|---|
| 5,957,864 A * | 9/1999 | Oosterhof | A61B 10/0283 600/562 |
| 6,258,064 B1 * | 7/2001 | Smith | A61B 17/3478 604/164.12 |
| 6,375,625 B1 * | 4/2002 | French | A61M 1/0001 600/573 |
| 7,517,321 B2 * | 4/2009 | McCullough | A61B 10/0275 600/562 |
| 7,871,383 B2 * | 1/2011 | Wiksell | A61B 10/0233 600/566 |
| 8,845,621 B2 * | 9/2014 | Fojtik | A61M 25/01 606/1 |
| 8,961,430 B2 * | 2/2015 | Coonahan | A61B 10/0275 600/564 |
| 9,265,485 B2 * | 2/2016 | Hibner | A61B 10/0275 |
| 2009/0131822 A1 | 5/2009 | Hibner et al. | |
| 2010/0292607 A1 | 11/2010 | Moore et al. | |
| 2010/0312140 A1 | 12/2010 | Smith et al. | |

* cited by examiner

*Primary Examiner* — Max Hindenburg
(74) *Attorney, Agent, or Firm* — Fox Rothschild LLP

(57) ABSTRACT

This application discloses aspiration/biopsy needle apparatus, devices containing these needle apparatus, and methods using these needle apparatus and devices for aspiration or biopsy of samples, in particular biological samples from mammalian subjects. The novel aspiration/biopsy needle systems can find wide applications in the manufacture of fine needle aspiration (FNA)/biopsy devices for convenient cell harvesting and tissue sampling and analysis.

38 Claims, 6 Drawing Sheets

ASPIRATION AND BIOPSY NEEDLE APPARATUS AND DEVICES AND APPLICATIONS THEREOF

CROSS REFERENCE TO RELATED APPLICATIONS

This application claims priority under 35 U.S.C. §119(e) to U.S. Provisional Application No. 61/983,213, filed on Apr. 23, 2014, which is incorporated herein by reference in its entirety.

FIELD OF THE INVENTION

This invention relates to aspiration needle devices and uses therefore, particularly their applications in the biopsy procedures to obtain biological samples.

BACKGROUND OF THE INVENTION

Biopsy devices for fine needle aspiration (FNA) are widely used for screening diagnostic procedures and are useful for obtaining cytological specimens for examination, for example, to confirm the diagnosis of a suspected medical condition. Typical specimens collected include liquids or cell samples. Such devices are generally useful in sampling tissue from breast, head and neck, lymph nodes, and for some gynecologic conditions. Other applications include lung, prostate, and other soft tissue biopsies.

Generally, biopsy devices of this type extract samples of tissue through a small needle in the range of 25-18 gauge. The needle is inserted, typically through the skin, so that the tip of the needle is in the suspect tissue mass. A vacuum force is applied by withdrawing the plunger of a standard syringe attached to the needle. To aid in harvesting an adequate sample size, the needle is optionally moved in and out of the puncture site a plurality of times. This reciprocating motion causes cellular material to be scraped from the tissue and drawn into the needle. This procedure draws up a small amount of tissue fluid, together with loose cells, into the syringe, and the collected specimen can be directly placed on a slide for pathological analysis.

Most existing FNA biopsy procedures use the regular needle-syringe systems, which are designed for the purpose of injection instead of aspiration biopsy, and therefore, have many limitations. After the procedure is done with a regular needle-syringe system, the specimen usually spreads all over the needle, needle-syringe joint, and/or inside of the syringe. Only a small fraction of the collected specimen could be directly placed on a slide usable for pathological analyses, and a major portion of the specimen is left in the needle and syringe. For additional analysis, the specimen has to be transferred into different containers through an extra procedure such as washing, which would cause substantial loss of the precious specimen as well as possible damages to the fresh specimen. Often, with the existing FNA needles, the procedure has to be repeated multiple times in order to obtain enough samples for the required analyses.

On the other hand, multiple biomarker identifications have become more and more important in the modern personalized medicines, especially in cancer diagnosis and treatment. Effective uses of a small quantity of biopsy specimen for multiple tests are highly desirable and often required. Therefore, aspiration and biopsy devices and methods capable of collecting maximally usable biological samples are in great need.

SUMMARY OF THE INVENTION

The present invention provides new aspiration/biopsy needle devices to meet the foregoing need, which can overcome the various shortcomings of the conventional sample collection methods mentioned above.

The fine needle aspiration biopsy devices described here are novel useful tools for the FNA biopsy procedures, which can be readily used to minimize the loss of and/or damages to the specimen collected, yet are suitable for use in the normal operations of the conventional procedures.

In one aspect the present invention provides an aspiration or biopsy device comprising: a body, a cannula needle, and a sample collection container, wherein:

the body comprises a vacuum channel and a plurality of ports;

the cannula needle comprises an inlet end positioned at a first port of the body, an outlet end positioned at a second port of the body, and a middle portion enclosed inside the body; and the vacuum channel of the body comprises a first opening end positioned at the second port of the body and a second opening end positioned at a third port of the body in communication with a vacuum source; and the sample collection container is coupled with the second port of the body, enclosing both of the outlet end of the cannula needle and the first opening end of the vacuum channel;

wherein the inlet end of the cannula needle is capable of aspirating a sample from a target when vacuum is applied on the second opening of the vacuum channel.

In another aspect the present invention provides a needle apparatus comprising a body and a cannula needle, wherein:

the body comprises a vacuum channel and a plurality of ports;

the cannula needle comprises an inlet end positioned at a first port of the body, an outlet end positioned at a second port of the body, and a middle portion enclosed inside the body; and the vacuum channel of the body comprises a first opening end and a second opening end, wherein the first opening end is positioned at the second port of the body so that the first opening end of the vacuum channel and the outlet end of the cannula needle can be contained in a same sample collection container coupled to the second port of the body, and the second opening end is positioned at a third port of the body, which can be in communication with a vacuum source.

In another aspect the present invention provides an aspiration device comprising a needle apparatus according to any one of the embodiments disclosed herein.

In another aspect the present invention provides a biopsy device comprising a needle apparatus according to any one of the embodiments disclosed herein.

In another aspect the present invention provides a method of extracting a biological sample from a subject, comprising: (1) providing a needle apparatus, an aspiration device, or a biopsy device according to any embodiment disclosed herein; (2) contacting the inlet end of the cannula needle of the device with a target of a desired biological sample; (3) applying a vacuum on the vacuum channel so that a desired biological sample is transferred through the cannula needle to a sample collection container.

In another aspect the present invention provides an aspiration method comprising:

a) providing an aspiration or biopsy device of any embodiment disclosed herein, or attaching a needle apparatus according to any embodiment disclosed herein to a sample collection container and a vacuum source; and b) aspirating a specimen through the needle inlet from a sample target into the sample collection container by applying a vacuum on the vacuum channel of the needle apparatus.

In one particular embodiment, the invention provides a fine needle aspiration (FNA) biopsy device for improved cell harvesting and a method of using the device. In one embodiment, the integrated fine needle aspiration (FNA) device comprises a detachable vial. In another embodiment, the integrated fine needle aspiration (FNA) device comprises a needle for penetration; an attached vial for receiving the specimen; and a syringe hub connector for attaching a vacuum source. In one embodiment, the syringe hub connector is a standard one. In another embodiment, the syringe hub connector is one having a specific size or shape to meet the need. In one embodiment, the vacuum source is a syringe, which can be a standard commercial one or a specifically designed one. In another embodiment, the vacuum source is a vacuum line optionally controlled by a vacuum gauge.

Among many other advantages, the aspiration needle system and the aspiration or biopsy devices of the present invention are easy to manufacture; convenient to assemble, dissemble, handle, and use, with each part easy to sterilize; and readily adaptable to different uses. All the parts of the apparatus or devices disclosed herein can be manufactured to fit the commercially readily available syringes, sample vials, needles, etc. manufactured according to the existing industrial standards. More importantly, the aspiration or biopsy methods using the system or devices of the present invention enable efficient extraction and use of biological samples while minimizing loss and damages to the specimens and preserving integrity of the specimens. The aspiration/biopsy devices capable of collecting maximally usable specimens will greatly benefit the clinical practices and the patients. Such devices are especially useful for extracting biological samples for early diagnosis of diseases, such as tumors, because the availability of samples is limited, and extraction of samples is difficult, at the early stage of the diseases.

These and other aspects of the present invention and advantages will become more apparent in view of the following drawings, detailed descriptions, and claims.

DETAILED DESCRIPTION OF THE INVENTION

Figure 1:
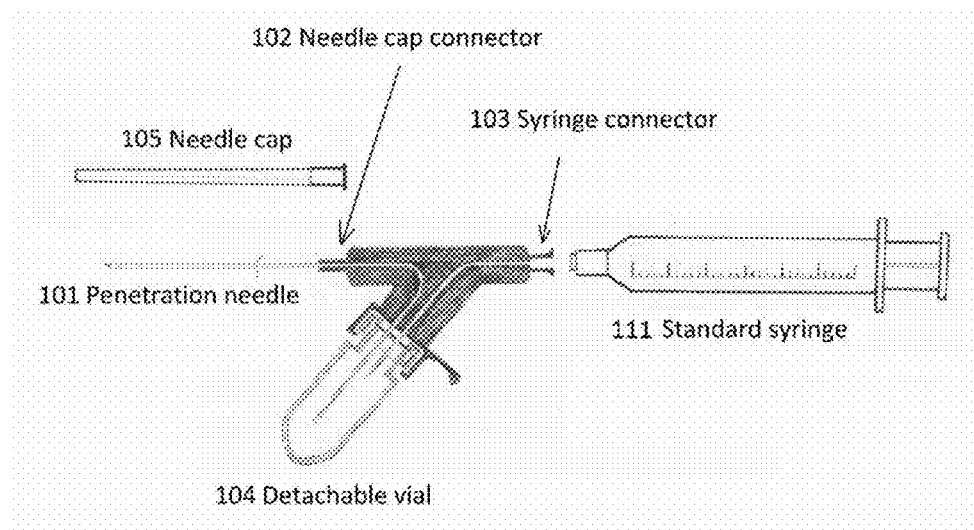
FIG. 1 illustrates a fine needle aspiration device of the present invention that can be connected with a syringe.

This invention, in one aspect, relates to fine needle aspiration (FNA) biopsy devices for improved cell harvesting and methods of using the devices, including but not limited to integrated fine needle aspiration (FNA) devices with detachable vials. For example, an integrated fine needle aspiration (FNA) device comprises a needle for penetration; an attached vial for receiving the specimen; and a standard syringe hub connector for attaching the vacuum source, such as a syringe. During the FNA biopsy procedure, the needle is inserted into a suspect tissue, a vacuum is created by a syringe or other vacuum sources, and cells and tissue from the targeted tissue mass are sucked through the needle into the attached vial. After the sample is obtained, the vial with the specimen sample can be detached from the device, and the sample is ready for examination.

Thus, in one aspect the present invention provides an aspiration or biopsy device comprising: a body, a cannula needle, and a sample collection container, wherein:

the body comprises a vacuum channel and a plurality of ports;

the cannula needle comprises an inlet end positioned at a first port of the body, an outlet end positioned at a second port of the body, and a middle portion enclosed inside the body; and the vacuum channel of the body comprises a first opening end positioned at the second port of the body and a second opening end positioned at a third port of the body in communication with a vacuum source; and the sample collection container is coupled with the second port of the body, enclosing both of the outlet end of the cannula needle and the first opening end of the vacuum channel;

wherein the inlet end of the cannula needle is capable of aspirating a sample from a target when vacuum is applied on the second opening of the vacuum channel.

In one embodiment of this aspect, the middle portion of the cannula needle is in airtight or substantially airtight contact with internal walls of the body surrounding the cannula needle.

In another embodiment of this aspect, the inlet and outlet ends of the cannula needle are two distinct pieces connected with each other through a connection means at the first port of the body.

In another embodiment of this aspect, the inlet end of the cannula needle comprises a detachable needle.

In another embodiment of this aspect, the inlet end piece comprises a needle of a commercially standard size and/or dimensions.

In another embodiment of this aspect, the inlet end of the cannula needle comprises a tip having a shape and dimension suitable for aspiration of a biological sample from an internal organ of a mammalian animal.

In another embodiment of this aspect, the second port of the body comprises a connection means to couple the body and the sample collection container.

In another embodiment of this aspect, the connection means is airtight or substantially airtight so that when a vacuum is applied on the vacuum channel, a sample can be aspirated by the inlet end of the cannula needle to the sample collection container.

In another embodiment of this aspect, the connection means fits a commercial sample collection container of standard size and/or dimensions.

In another embodiment of this aspect, the connection means is a clip mechanism, a screw mechanism, or a combination thereof.

In another embodiment of this aspect, the sample collection container is a disposable commercial sample vial.

In another embodiment of this aspect, the sample collection container is a centrifugation tube.

In another embodiment of this aspect, the inlet end of the cannula needle is protected by a cover.

In another embodiment of this aspect, the protection cover of the inlet end of the cannula needle comprises a plastic sheath.

In another embodiment of this aspect, the vacuum source comprises a means for generating a vacuum.

In another embodiment of this aspect, the means for generating a vacuum is selected from a vacuum pump, a syringe, an adaptor to connect with a vacuum line, or a combination thereof.

In another embodiment of this aspect, the vacuum source comprises a syringe.

In another embodiment of this aspect, the syringe is connected with the third port of the body through a connecting means so that the syringe can directly apply vacuum on the second opening end of the vacuum channel.

In another embodiment of this aspect, the connecting means is airtight or substantially airtight.

In another embodiment of this aspect, the connecting means is selected from clip mechanisms, screw mechanisms, and combinations thereof. In a preferred embodiment, the connection means is a standard syringe hub connector.

In another embodiment of this aspect, the connecting means is a standard screw that fits with a commercial syringe of standard size and dimensions.

In another embodiment of this aspect, the syringe is a disposable one.

In another embodiment of this aspect, the vacuum channel further comprises a vacuum duct enclosed inside and attached to the internal wall of the channel.

In another embodiment of this aspect, the vacuum duct comprises two opening ends extending outside the channel, wherein one opening end extends to the sample collection container, and the other opening end is in communication with a vacuum source.

In another embodiment of this aspect, the vacuum duct is a cannula needle, a metal tubing, or a plastic tubing.

In another embodiment of this aspect, the opening end of the vacuum duct in the sample collection container is at a distance from the opening of the outlet end of the cannula needle so that they are not in proximity with each other to prevent the sample collected from entering the vacuum duct.

In another embodiment of this aspect, the portion of the vacuum duct in the sample collection container is shorter than the outlet end of the cannula needle in the sample collection container.

In another embodiment of this aspect, the vacuum duct comprises a cannula needle having a sharp tip at the opening end in the sample collection container so that it can penetrate a rubber cap or stopper of a sample collection container.

In another embodiment of this aspect, at least one or two of the sample inlet needle piece, the sample collection container, and the vacuum source are provided separately in sterilized containers, respectively, from the body, and the device can be assembled right before use.

In another embodiment of this aspect, the device is pre-assembled and stored in a sterilized container ready for use.

In another embodiment of this aspect, all the parts of the aspiration device are disposable after a single use.

In another embodiment of this aspect, the aspiration device is a fine needle aspiration (FNA) device.

In another aspect the present invention provides a needle apparatus comprising a body and a cannula needle, wherein:

the body comprises a vacuum channel and a plurality of ports;

the cannula needle comprises an inlet end positioned at a first port of the body, an outlet end positioned at a second port of the body, and a middle portion enclosed inside the body; and the vacuum channel of the body comprises a first opening end and a second opening end, wherein the first opening end is positioned at the second port of the body so that the first opening end of the vacuum channel and the outlet end of the cannula needle can be contained in a same sample collection container coupled to the second port of the body, and the second opening end is positioned at a third port of the body, which can be in communication with a vacuum source.

In one embodiment of this aspect, the middle portion of the cannula needle is in airtight or substantially airtight contact with internal wall of the body surrounding the cannula needle so that the inlet end of the cannula needle can extract a sample from a target when a sample collection container is coupled to the second port of the body, enclosing both of the outlet end of the cannula needle and the first opening end of the vacuum channel, and a vacuum is applied on the second opening end of the vacuum channel at the third port.

In another embodiment of this aspect, the vacuum channel further comprises a vacuum duct enclosed inside and attached to the internal wall of the channel.

In another embodiment of this aspect, the vacuum duct comprises two opening ends extending outside the channel, wherein one opening end extends to the sample collection container, and the other opening end is in communication with a vacuum source.

In another embodiment of this aspect, the vacuum duct is a cannula needle, a metal tubing, or a plastic tubing.

In another embodiment of this aspect, the opening end of the vacuum duct in the sample collection container is at a distance from the opening of the outlet end of the cannula needle so that they are not in proximity with each other to prevent the sample collected from entering the vacuum duct.

In another embodiment of this aspect, the portion of the vacuum duct in the sample collection container is shorter than the outlet end of the cannula needle in the sample collection container.

In another embodiment of this aspect, the vacuum duct comprises a cannula needle having a sharp tip at the opening end in the sample collection container so that it can penetrate a rubber cap or stopper of a sample collection container.

In another embodiment of this aspect, the inlet and outlet ends of the cannula needle comprise two distinct pieces connected with each other through a connecting means between the inlet end needle and the first port of the body.

In another embodiment of this aspect, the inlet end piece of the cannula needle is a replaceable needle.

In another embodiment of this aspect, the inlet end piece is a commercial needle of standard size and dimensions for aspiration of biological samples.

In another embodiment of this aspect, the inlet end of the cannula needle comprises a sampling tip of a size and shape suitable for aspiration of a biological sample from a mammalian subject.

In another embodiment of this aspect, the second port of the body comprises a connection means to couple with a sample collection container.

In another embodiment of this aspect, the connection means is airtight or substantially airtight so that when a vacuum is applied on the vacuum channel, a biological sample can be aspirated by the inlet end of the cannula needle.

In another embodiment of this aspect, the connection means fits a standard commercial sample vial.

In another embodiment of this aspect, the airtight connection means comprises a clip mechanism, a screw mechanism, or a combination thereof.

In another embodiment of this aspect, the sample collection container is a disposable commercial sample vial.

In another embodiment of this aspect, the sample collection container is a centrifugation tube.

In another embodiment of this aspect, the apparatus further comprises a cover to protect the inlet end of the cannula needle.

In another embodiment of this aspect, the protection cover at the inlet end of the cannula needle is a plastic sheath.

In another embodiment of this aspect, the vacuum source is selected from a vacuum pump, a syringe, and an adapter connected with a vacuum line, or a combination thereof.

In another aspect the present invention provides an aspiration/biopsy device comprising a needle apparatus according to any one of the embodiments disclosed herein.

In one embodiment of this aspect, the aspiration device further comprises a sample collection container, wherein said sample collection container is coupled to the second port of the body of the needle apparatus and encloses the outlet end of the cannula needle and the first opening end of the vacuum channel.

In another embodiment of this aspect, the aspiration device further comprises a vacuum source connected to the second opening end of the vacuum channel.

In another embodiment of this aspect, the vacuum source is a syringe.

In another embodiment of this aspect, the syringe is connected to the third port of the body through a connecting means.

In another embodiment of this aspect, the connecting means is a clip mechanism, a screw mechanism, or a combination thereof. In a preferred embodiment, the connection means is a standard syringe hub connector.

In another aspect the present invention provides an aspiration/biopsy device comprising a needle apparatus according to any one of the embodiments disclosed herein.

In one embodiment of this aspect, the biopsy device further comprises a sample collection container, wherein said sample collection container is coupled to the second port of the body of the needle apparatus and encloses the outlet end of the cannula needle and the first opening end of the vacuum channel.

In another embodiment of this aspect, the biopsy device further comprises a vacuum source connected to the second opening end of the vacuum channel.

In another embodiment of this aspect, the vacuum source is a syringe.

In another embodiment of this aspect, the syringe is connected to the third port of the body through a connecting means.

In another embodiment of this aspect, the connecting means is a clip mechanism, a screw mechanism, or a combination thereof. In a preferred embodiment, the connection means is a standard syringe hub connector.

In another aspect the present invention provides a method of extracting a biological sample from a subject, comprising: (1) providing a needle apparatus, an aspiration device, or a biopsy device according to any embodiment disclosed herein; (2) contacting the inlet end of the cannula needle of the device with a target of a desired biological sample; (3) applying a vacuum on the vacuum channel so that a desired biological sample is transferred through the cannula needle to a sample collection container.

In one embodiment of this aspect, the method further comprises (4) rinsing the cannula needle with a liquid to transfer the residue of the sample from the cannula needle to the sample collection container.

In another embodiment of this aspect, the sample collection container is a glass or plastic vial or a glass or plastic centrifugation tube.

In another embodiment of this aspect, the target of the biological sample is an organ of a subject or another biological sample.

In another embodiment of this aspect, the biological sample is a block of cells, a solid tissue, or a fluid.

In another embodiment of this aspect, the solid tissue is a tumor tissue.

In another embodiment of this aspect, the sample target is an internal organ or a mammalian animal, such as a human, a dog, a cat, a horse, or the like.

In another aspect the present invention provides an aspiration method comprising:

a) providing an aspiration or biopsy device of any embodiment disclosed herein, or attaching a needle apparatus according to any embodiment disclosed herein to a sample collection container and a vacuum source; and b) aspirating a specimen through the needle inlet from a sample target into the sample collection container by applying a vacuum on the vacuum channel of the needle apparatus.

In one embodiment of this aspect, the step b) further comprises rinsing residue of the biological sample from the cannula needle into the sample collection container by contacting the inlet end of the cannula needle with a rinsing liquid and applying a vacuum on the vacuum channel of the needle apparatus in a controlled amount.

In another embodiment of this aspect, the method further comprises c) detaching the sample collection container from the body of the aspiration or biopsy device or the needle apparatus.

In another embodiment of this aspect, the sample collection container is an analytical sample vial ready for analysis.

In another embodiment of this aspect, the sample collection container is a centrifugation tube, and the method further comprises d) concentrating the sample solution by centrifugation.

The needle apparatus and devices thereof according to the present invention are versatile and adaptable for different uses, for example, aspiration of fluid samples and biopsy of soft tissues, by varying design of the needle. For example, fluid biological samples can be readily extracted using regular disposable needle; and using a needle having a tip suitable for scraping soft tissues or even bone samples, the devices can be used for biopsy of those solid samples. The flexibility makes the devices especially useful for bone marrow aspiration or biopsy procedures as well as biopsy of various solid tumors, such as breast, head and neck, prostate, lung, stomach, liver, and brain cancers, and melanomas, etc.

The dimensions and specifications of the devices and apparatus disclosed herein can be adjusted to suit any particular use for extraction of biological samples, as a person skilled in the art will be able to do based on the disclosure and known practice in the medical field. For example, thickness, internal diameter, and lengths of the middle portion and the inlet and outlet ends of the needles can be adjusted based on the need and procedures in which the device or apparatus is used, as well as conditions under which the procedure takes place, which may include, but are not limited to, the source of the biological sample to be extracted, the nature and property of the biological sample to be extracted, and the amount to be extracted, etc.

In the present invention, the same device or apparatus may be suitable for use in both aspiration of liquid samples and biopsy of soft tissue or solid tissue samples by altering dimensions and/or shape of the specifications, for example, in particular, the tip of the inlet end of the cannula needle, as would be grasped by those skilled in the art. In this aspect, the detachable needle in the inlet end is particular desirable so that it can be changed readily, sterilized, and reused.

In some embodiments, the terms "aspiration" and "biopsy" may be interchangeable for the purpose of the present invention, and thus they may be collectively called "extraction" of a biological sample. The term "target" or "source", or the like, of a biological sample in a "subject", as used herein refers to an organ, tissue, blood, or any body part of a mammalian animal, preferably a human.

Although it would be preferable to have all or most of the connection means mentioned in the application meet the existing industrial standards so that they would be convenient to use and can avoid unnecessary special manufacturing costs, nevertheless, in principle, they can be manufactured customarily for different purposes without any specific limitations.

EXAMPLES

The following non-limiting examples of certain embodiments are provided to further illustrate certain aspects of the present invention.

Figure 2:
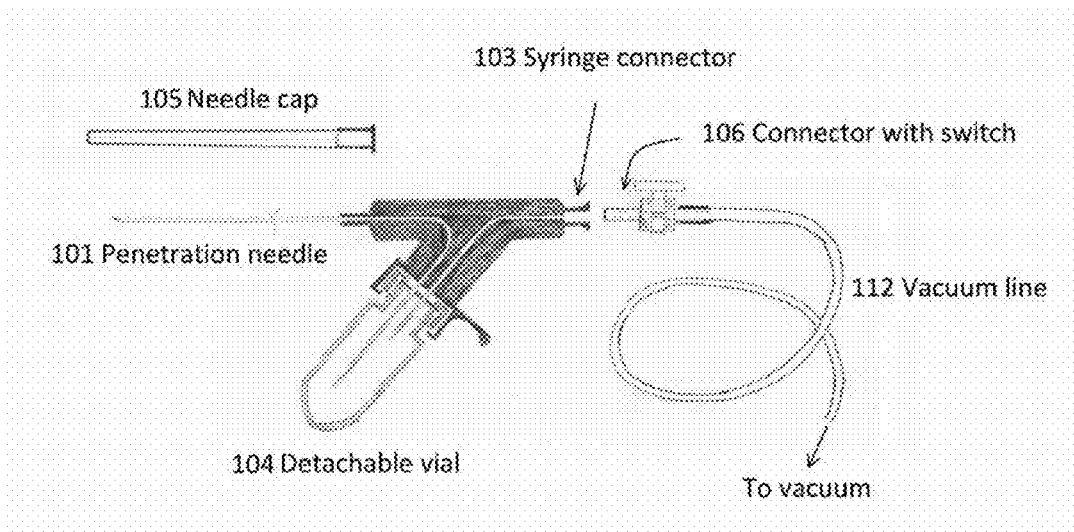
FIG. 2 illustrates a fine needle aspiration device that can be connected with a vacuum line.

Some needle aspiration devices for obtaining tissue samples are illustrated in FIG. 1 and FIG. 2. These devices may be used in substantially all procedures employing conventional FNA devices and further increase the efficiency of FNA procedures with minimum loss of the collected specimen.

Figure 3:
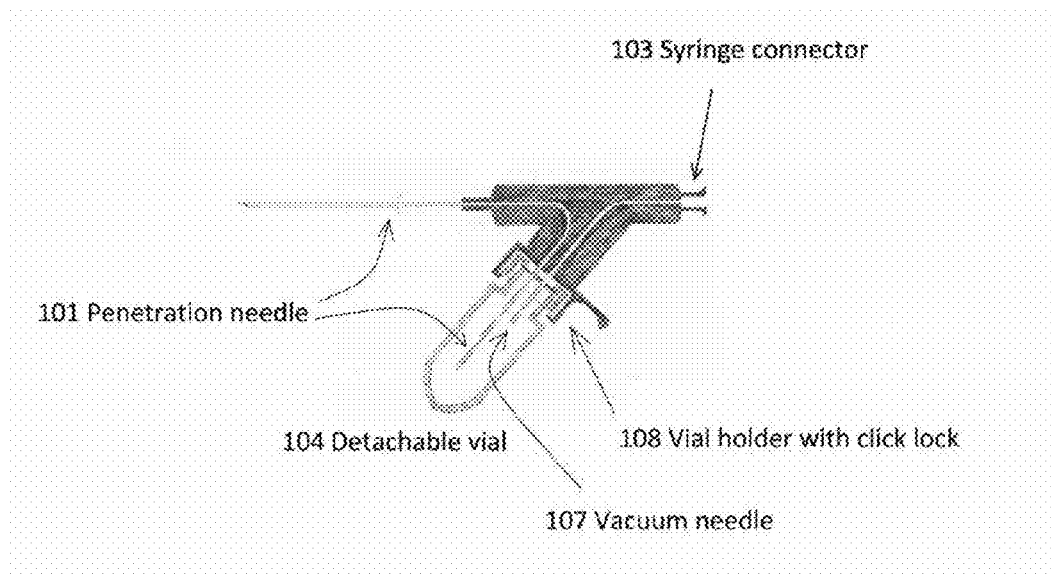
FIG. 3 illustrates a main center piece of the fine needle aspiration device.

As illustrated in FIG. 3, the invention of the integrated fine needle aspiration (FNA) device comprises a cannula penetration needle 101 with one sharp end for the penetration of the targeted tissue, and the other end inside the attached receiving vial 104. During the procedure, the sharp tip of the penetration needle 101 penetrates into the target tissue mass and extracts a small amount of the tissue and cells by utilizing an in-and-out motion. The tissue fluid, together with loose tiny pieces of tissues and cells, is drawn directly into the attached receiving vial 104 through the cannula penetration needle 101.

Figure 4:
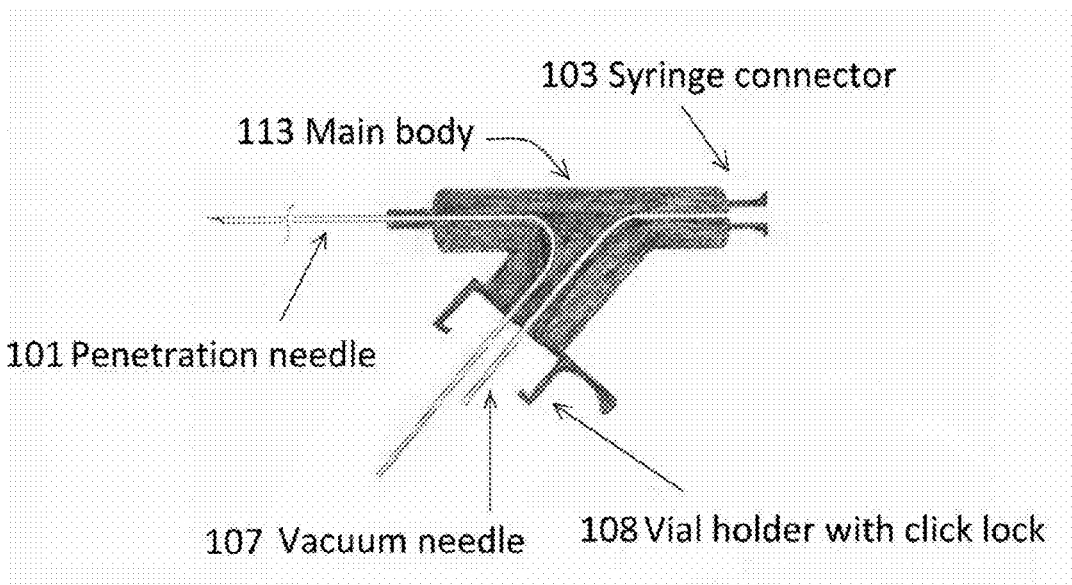
FIG. 4 illustrates a fine needle aspiration device without attachments.
Figure 5:
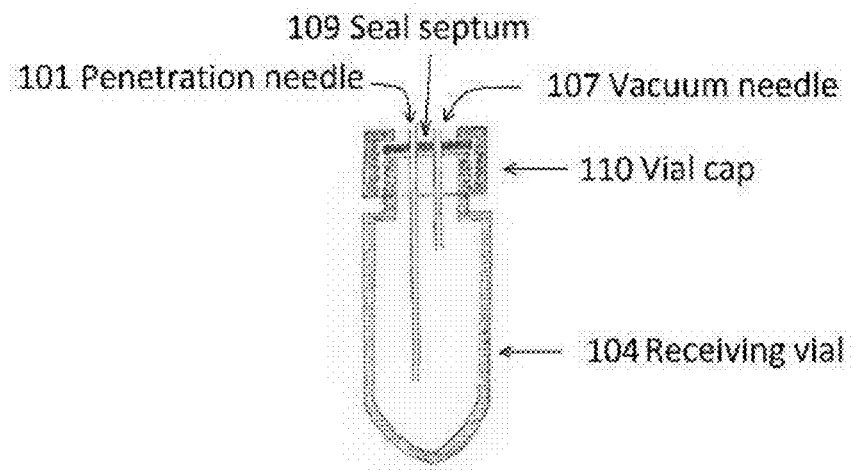
FIG. 5 illustrates an example of receiving vial for the fine needle aspiration device.

As illustrated in FIG. 3, the invention of the integrated fine needle aspiration (FNA) device comprises also a vial holder with 108, such as a click lock, through which, a receiving vial 104 is attached. The receiving vial 104 can be the common centrifuge vials with cap 110 that has a hole and a penetrable PTFE/silicone seal septum 109 as illustrated in FIG. 4. The vial holder 108 has two needle outlets. The first needle outlet is the other end of the cannula of the penetration needle 101, through which the specimen is guided into the receiving vial 104. The second needle outlet is the end of the cannula of the vacuum needle 107. Or in other embodiments, the second needle outlet is connected to a vacuum line through a tubing, duct, or the like. During the procedure, vacuum is generated inside the receiving vial 104 through the vacuum needle 107 by either a syringe 111 as illustrated in FIG. 1, or by other vacuum sources such as vacuum line 112 as illustrated in FIG. 2. The vial holder 108 has also a build-in click lock, which holds the receiving vial 104 in place during the procedure. The receiving vial 104 can be easily detached from the vial holder 108 with release of the click lock after the procedure. The specimen in the receiving vial 104 can be directly used for analysis. If desired, the specimen trapped inside the cannula of the penetration needle 101 can be washed into the receiving vial 104 by drawing a small quantity of proper washing buffer solution through the penetration needle 101 before detaching the receiving vial 104.

As illustrated in FIG. 3, the invention of the integrated fine needle aspiration (FNA) device comprises also a syringe connector 103, which can be of a standard or non-standard size. For economic and convenience reasons, in some preferred embodiments, the syringe connector is of standard sizes so as to fit different standard sizes of syringes. A common standard syringe 111 can connected to the universal connector 103 as illustrated in FIG. 1, and the biopsy procedure can be performed in the same way as the conventional FNA biopsy. Furthermore, through this universal standard syringe connector 103, various vacuum sources, such as a standard syringe-needle connector 106 with a tube linked to the in-house vacuum port, can be connected to the FNA device of the current invention as illustrated in FIG. 2. The biopsy procedure can be performed easily by directly handling the device without withdrawing the plunger of the syringe.

During the FNA biopsy procedure, the needle is inserted into the suspect tissue, a vacuum is created by the syringe or other vacuum sources, and cells and tissue from the targeted mass are sucked through the needle into the attached vial. When the sample is obtained, the vial with the specimen sample is detached from the device and ready for examination.

Figure 6:
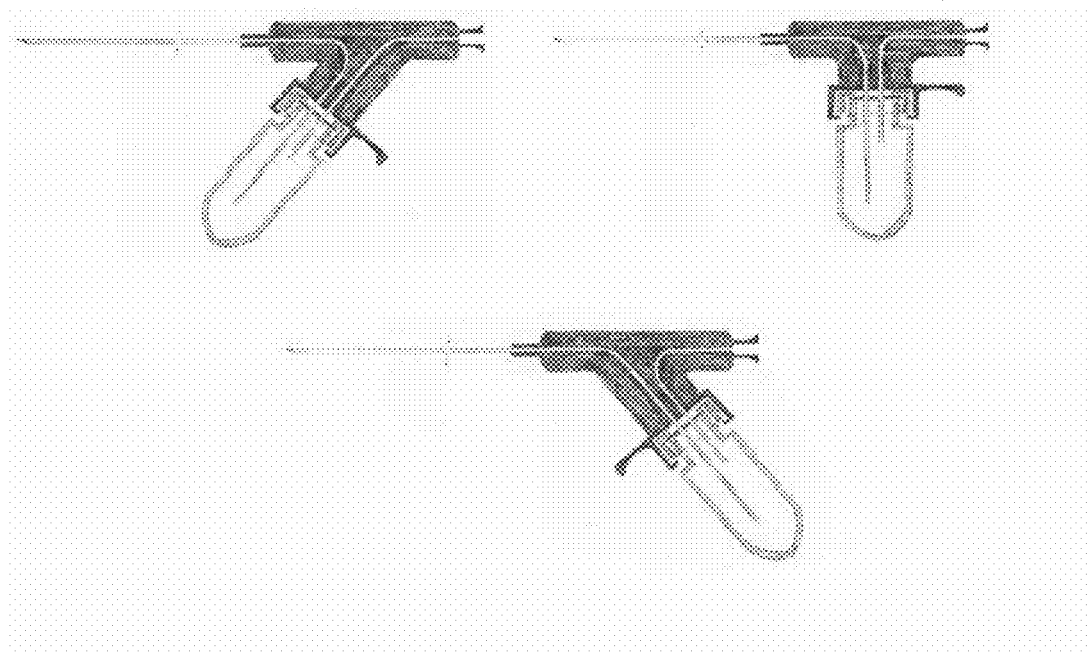
FIG. 6 illustrates the fine needle aspiration devices in various example shapes.

As illustrated in FIG. 6, the receiving vial can be orientated to different angles to fit different biopsy positions for easy handling and preventing the sample from being sucked into the vacuum needle.

Figure 7:
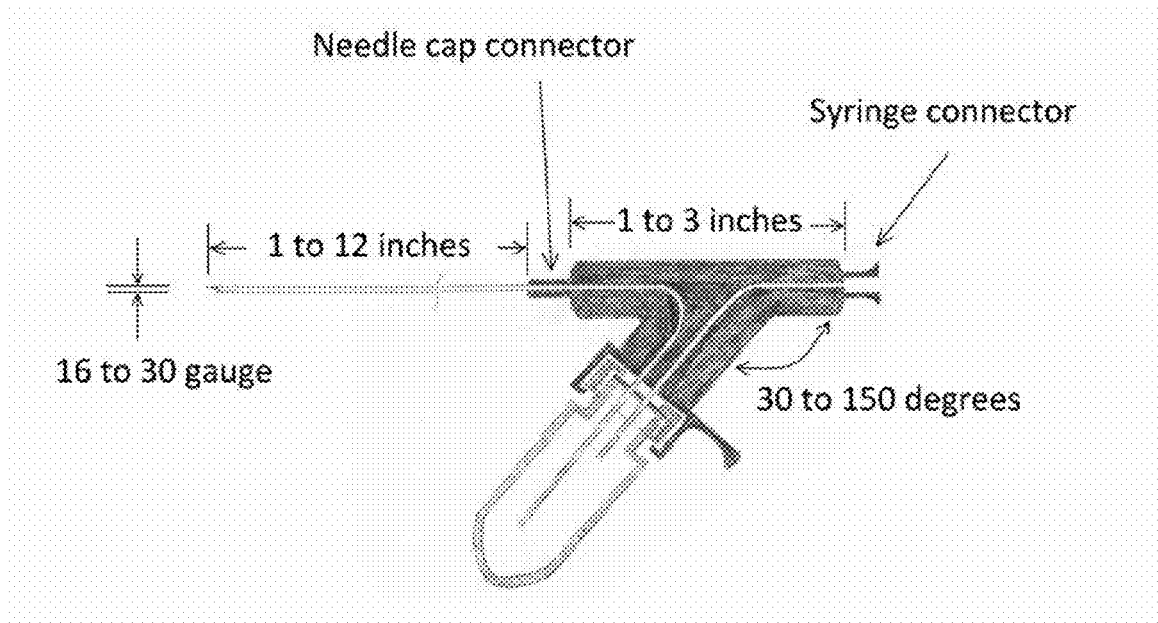
FIG. 7 illustrates various example dimensions of the fine needle aspiration devices.
Figure 8:
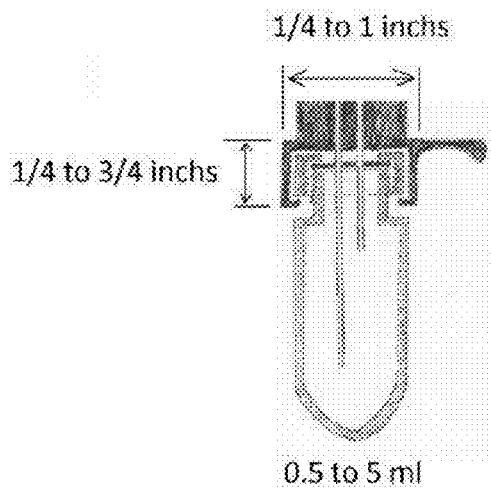
FIG. 8 illustrates example dimensions of receiving vials for the fine needle aspiration devices.

As illustrated in FIG. 7, the penetration needle 101 can vary in size from 30-16 gauge, and 1 to 12 inch long to meet different needs for the different type of the target tissue and organs. The main body 113 of the device can also vary in size, such as from 1 inch to 3 inches. The smaller size, such as 1 inch, is for the device that is connected to a syringe as illustrated in FIG. 1. The larger size, such as 3 inches, is for the device that is connected to a vacuum line as illustrated FIG. 2 for easy manual handling. The size of the vial holder 108 can be ¼ to 1 inches in diameter and ¼ to ¾ inches in depth to fit the most commonly used receiving vials 104. The size of the receiving vial 104 can range from 0.5 ml to 5 ml depend on the sample types and sizes. Small sized receiving vial is for the biopsy of small quantity of solid tissue samples, while the larger receiving vial is for the fluid samples, which is frequently in relative larger volume.

Figure 9:
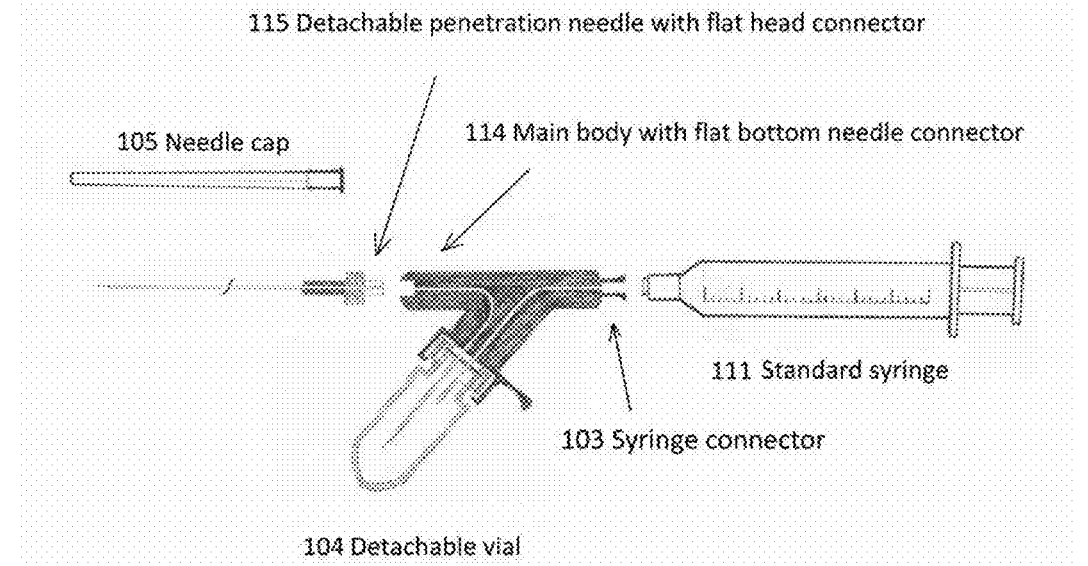
FIG. 9 illustrates an example of the fine needle aspiration device with a detachable penetration needle.
Figure 10:
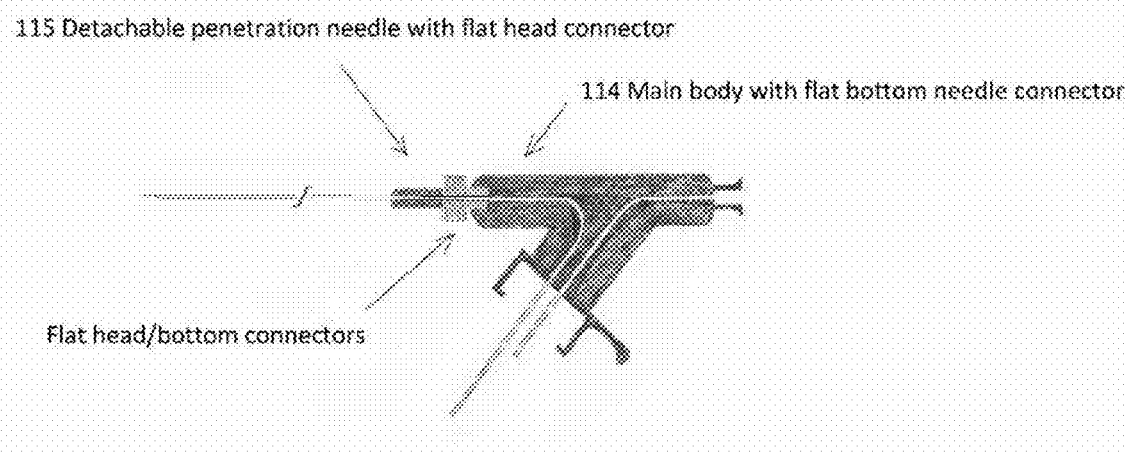
FIG. 10 illustrates an example of the fine needle aspiration device connected with a detachable penetration needle.

As illustrated in FIG. 9, the invention of the integrated fine needle aspiration (FNA) device can be modified to comprise also a detachable penetration needle 115. The detachable penetration needle 115 has a flat head connector, which can be tightly connected to the flat bottom needle connector of the main FNA body 114. The connectors were designed with tightly matched flat head/bottom connection to eliminate the dead space inside the connectors as illustrated in FIG. 10.

Figure 11:
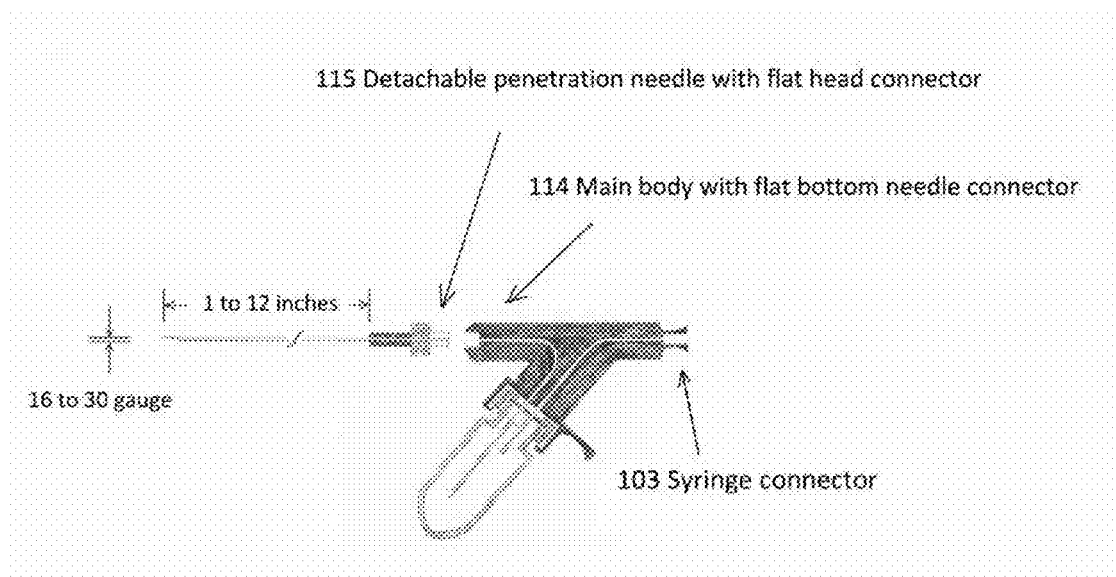
FIG. 11 illustrates example dimensions of a detachable needle suitable for the fine needle aspiration devices.

As illustrated in FIG. 11, the detachable penetration needle 115 can vary in size from 30-16 gauge, and 1 to 12 inch long to meet different needs for the different type of the target tissue and organs.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the following claims.

What is claimed is:

1. An aspiration/biopsy device comprising: a body, a cannula needle, and a sample collection container, wherein:
    the body comprises a vacuum channel and a plurality of ports;
    the cannula needle traverses inside the body, comprising an inlet end positioned at and extending from a first port of the body, an outlet end positioned at and extending from a second port of the body, and a middle portion enclosed inside the body;
    the vacuum channel traverses inside the body, comprising a first opening end positioned at the second port of the body and a second opening end positioned at a third port of the body in communication with a vacuum source; and
    the sample collection container is coupled with the second port of the body, enclosing both of the outlet end of the cannula needle and the first opening end of the vacuum channel;
    wherein the inlet end of the cannula needle is capable of extracting a biological sample from a subject when vacuum is applied on the second opening of the vacuum channel.

2. The aspiration/biopsy device of claim 1, wherein said middle portion of the cannula needle is in airtight or substantially airtight contact with internal walls of the body surrounding the middle portion of the cannula needle.

3. The aspiration/biopsy device of claim 1, wherein the inlet and outlet ends of the cannula needle are two distinct pieces connected with each other through a connection means at the first port of the body.

4. The aspiration/biopsy device of claim 3, wherein the inlet end of the cannula needle comprises a detachable needle.

5. The aspiration/biopsy device of claim 1, wherein the second port of the body comprises a connection means to couple the body and the sample collection container.

6. The aspiration/biopsy device of claim 5, wherein the connection means is airtight or substantially airtight so that when a vacuum is applied on the vacuum channel, a sample can be extracted by the inlet end of the cannula needle to the sample collection container.

7. The aspiration/biopsy device of claim 5, wherein the connection means is a clip mechanism, a screw mechanism, or a combination thereof.

8. The aspiration/biopsy device of claim 1, wherein the sample collection container is a sample vial or centrifugation tube.

9. The aspiration/biopsy device of claim 1, wherein said vacuum source is a vacuum pump, a syringe, a vacuum line, or a combination thereof.

10. The aspiration/biopsy device of claim 1, wherein the vacuum source comprises a syringe.

11. The aspiration/biopsy device of claim 10, wherein the syringe is connected with the third port of the body through a connecting means so that the syringe can directly apply vacuum on the second opening end of the vacuum channel.

12. The aspiration/biopsy device of claim 11, wherein the connecting means is airtight or substantially airtight.

13. The aspiration/biopsy device of claim 11, wherein the connecting means is selected from clip mechanisms, screw mechanisms, and combinations thereof.

14. The aspiration/biopsy device of claim 1, wherein the vacuum channel further comprises a vacuum duct enclosed inside and attached to the internal wall of the channel.

15. The aspiration/biopsy device of claim 14, wherein the vacuum duct comprises two opening ends extending outside the channel, wherein one opening end extends to the sample collection container, and the other opening end is in communication with a vacuum source.

16. The aspiration/biopsy device of claim 14, wherein the vacuum duct is a cannula needle, a metal tubing, or a plastic tubing.

17. The aspiration/biopsy device of claim 14, wherein the vacuum duct comprises a cannula needle having a sharp tip at the opening end in the sample collection container so that it can penetrate a rubber cap or stopper of a sample collection container.

18. The aspiration/biopsy device of claim 1, which is a fine needle aspiration (FNA) device.

19. A needle apparatus comprising a body and a cannula needle, wherein:
    the body comprises a vacuum channel and a plurality of ports;
    the cannula needle traverses inside the body, comprising an inlet end positioned at a first port of the body, an outlet end positioned at a second port of the body, and a middle portion enclosed inside the body; and
    the vacuum channel traverses inside the body, comprising a first opening end and a second opening end, wherein the first opening end is positioned at the second port of the body so that the first opening end of the vacuum channel and the outlet end of the cannula needle can be contained in a same sample collection container coupled to the second port of the body, and the second opening end is positioned at a third port of the body, which can be in communication with a vacuum source.

20. The needle apparatus of claim 19, wherein said middle portion of the cannula needle is in airtight or substantially airtight contact with internal wall of the body surrounding the cannula needle so that the inlet end of the cannula needle can extract a sample from a target when a sample collection container is coupled to the second port of the body, enclosing both of the outlet end of the cannula needle and the first opening end of the vacuum channel, and a vacuum is applied on the second opening end of the vacuum channel at the third port.

21. The needle apparatus of claim 19, wherein the inlet and outlet ends of the cannula needle comprise two distinct pieces connected with each other through a connecting means between the inlet end needle and the first port of the body.

22. The needle apparatus of claim 21, wherein the inlet end piece of the cannula needle is a replaceable needle.

23. The needle apparatus of claim 19, wherein the inlet end of the cannula needle comprises a sampling tip of a size and shape suitable for aspiration of a biological sample from a mammalian subject.

24. The needle apparatus of claim 19, wherein the second port of the body comprises a connection means to couple with a sample collection container.

25. The needle apparatus of claim 24, wherein the connection means is airtight or substantially airtight so that when a vacuum is applied on the vacuum channel, a biological sample can be extracted by the inlet end of the cannula needle.

26. The needle apparatus of claim 24, wherein the airtight connection means comprises a clip mechanism, a screw mechanism, or a combination thereof.

27. The needle apparatus of claim 19, wherein the vacuum source is selected from a vacuum pump, a syringe, and an adapter connected with a vacuum line, or a combination thereof.

28. An aspiration/biopsy device comprising a needle apparatus of claim 19.

29. The aspiration/biopsy device of claim 28, further comprising a sample collection container, wherein said sample collection container is coupled to the second port of the body of the needle apparatus and encloses the outlet end of the cannula needle and the first opening end of the vacuum channel.

30. The aspiration/biopsy device of claim 29, further comprising a syringe coupled to the third port of the body through a connecting means to enclose the second opening end of the vacuum channel.

31. The aspiration/biopsy device of claim 30, wherein said connecting means is a clip mechanism, a screw mechanism, or a combination thereof.

32. A method of extracting a biological sample from a subject, comprising: (1) providing an aspiration or biopsy device comprising a needle apparatus of claim 19; (2) contacting the inlet end of the cannula needle of said needle apparatus with a target of a desired biological sample; (3) applying a vacuum on the vacuum channel of said needle apparatus so that the desired biological sample is transferred through the cannula needle to a sample collection container.

33. The method of claim 32, further comprising (4) rinsing the cannula needle with a liquid to transfer the residue of the sample from the cannula needle to the sample collection container.

34. The method of claim 32, wherein the sample collection container is sample correction vial or centrifugation tube.

35. The method of claim 32, wherein said biological sample is a block of cells, a solid tissue, or a fluid.

36. An aspiration/biopsy method comprising:
a) providing an aspiration or biopsy device of claim 1 attached to a vacuum source; and b) extracting a specimen through the needle inlet from a sample target into the sample collection container by applying a vacuum on the vacuum channel of the needle apparatus.

37. The aspiration/biopsy method of claim 36, wherein the step b) further comprises rinsing residue of the biological sample from the cannula needle into the sample collection container by contacting the inlet end of the cannula needle with a rinsing liquid and applying a vacuum on the vacuum channel of the needle apparatus in a controlled amount.

38. The aspiration/biopsy method of claim 36, further comprising c) detaching the sample collection container from the body of the aspiration or biopsy device or the needle apparatus.

* * * * *